United States Patent [19]

Kampe et al.

[11] 4,146,630
[45] Mar. 27, 1979

[54] BLOOD PRESSURE LOWERING AND ADRENERGIC β-RECEPTOR INHIBITING 3-(4-PHENOXYMETHYLPIPERIDINO)-PROPYL-PHENYL ETHERS

[75] Inventors: Wolfgang Kampe, Heddesheim; Walter-Gunar Friebe, Darmstadt; Fritz Wiedemann, Weinheim-Lützelsachsen; Gisbert Sponer, Hemsbach; Wolfgang Bartsch, Viernheim; Karl Dietmann, Mannheim-Vogelstang, all of Fed. Rep. of Germany

[73] Assignee: Boehringer Mannheim GmbH, Mannheim, Fed. Rep. of Germany

[21] Appl. No.: 846,057

[22] Filed: Oct. 27, 1977

[30] Foreign Application Priority Data

Nov. 12, 1976 [DE] Fed. Rep. of Germany ....... 2651574
Aug. 20, 1977 [DE] Fed. Rep. of Germany ....... 2737630

[51] Int. Cl.² .................. A61K 31/445; C07D 401/12
[52] U.S. Cl. ................................... 424/267; 546/199; 546/201; 546/230; 546/232; 546/235; 546/234; 546/238; 546/239; 546/240; 546/236; 546/207; 546/237; 260/308 B; 548/325; 548/371
[58] Field of Search .......... 260/293.59, 293.6, 293.61; 424/267

[56] References Cited

U.S. PATENT DOCUMENTS 3,287,461 11/1966 Gray ................................ 260/293.61
3,699,123 10/1972 Seemann et al. ................ 260/293.61

FOREIGN PATENT DOCUMENTS 1404003 8/1975 United Kingdom ................ 260/293.61

OTHER PUBLICATIONS

Chemical Abstracts, 56:11560c (1962) [Gray, A. et al., J. Org. Chem. 26, 3368-3373 (1961)].

Primary Examiner—Henry R. Jiles
Assistant Examiner—Richard A. Schwartz
Attorney, Agent, or Firm—Sprung, Felfe, Horn, Lynch & Kramer

[57] ABSTRACT

A 3-(4-phenoxymethylpiperidino)-propyl-phenyl-ether of the formula

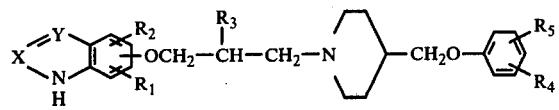

wherein
$R_1$ and $R_2$ each independently is hydrogen, lower alkyl, hydroxyalkyl, lower alkanoyloxyalkyl or —CO—Z,
Z is hydroxy, lower alkyloxy or

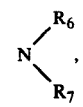

$R_6$ and $R_7$ each independently is hydrogen, lower alkyl or hydroxyalkyl,
$R_3$ is hydrogen or —O—$R_8$,
$R_8$ is hydrogen, lower alkanoyl or aroyl optionally substituted by halogen, lower alkyl, lower alkoxy, alkoxycarbonyl, hydroxyl, alkylthio, nitrile, nitro or trifluoromethyl,
$R_4$ and $R_5$ each independently is hydrogen, halogen, hydroxy, benzyloxy, lower alkyl, lower alkoxy, lower alkylthio, carboxy, benzyloxycarbonyl or lower alkoxycarbonyl,
X and Y each independently is nitrogen or

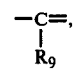

$R_9$ is hydrogen, lower allkyl optionally substituted by —O—$R_8$, or —CO—Z,
or a pharmacologically acceptable salt thereof. The compounds lower blood pressure and inhibit adrenergic β-receptors.

12 Claims, No Drawings

BLOOD PRESSURE LOWERING AND ADRENERGIC β-RECEPTOR INHIBITING 3-(4-PHENOXYMETHYLPIPERIDINO)-PROPYL-PHENYL ETHERS

The present invention is concerned with new piperidinopropyl derivatives and with the preparation thereof.

The new piperidinopropyl derivatives according to the present invention are compounds of the general formula:

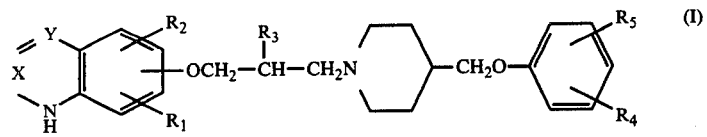

wherein $R_1$ and $R_2$, which can be the same or different, are hydrogen atoms, lower alkyl radicals, hydroxyalkyl radicals, lower alkanoyloxyalkyl radicals or —CO-Z groups, Z being a hydroxy group, a lower alkoxy radical or an

radical, in which $R_6$ and $R_7$, which can be the same or different, are hydrogen atoms, lower alkyl radicals or hydroxyalkyl radicals, $R_3$ is a hydrogen atom or an —O—$R_8$ radical, $R_8$ being a hydrogen atom, a lower alkanoyl radical or an aroyl radical which is optionally substituted by halogen, lower alkyl, lower alkoxy, alkoxycarbonyl, hydroxyl, alkylthio, nitrile, nitro or trifluoromethyl, $R_4$ and $R_5$, which can be the same or different, are hydrogen or halogen atoms, hydroxyl groups, benzyloxy radicals, lower alkyl radicals, lower alkoxy radicals, lower alkylthio radicals, carboxyl groups, benzyloxycarbonyl radicals or lower alkoxycarbonyl radicals, X and Y, which can be the same or different, are nitrogen atoms or

radicals, $R_9$ being a hydrogen atom or a lower alkyl radical, which is optionally substituted by an —O—$R_8$ radical, $R_8$ having the same meaning as above, or a —CO-Z group, Z having the same meaning as above; and the pharmacologically acceptable salts thereof.

Since, insofar as $R_3$ is other than a hydrogen atom, the compounds of general formula (I) possess an asymmetrical carbon atom, the present invention also includes the optically-active forms and the racemic mixtures of these compounds.

The compounds of general formula (I) and the pharmacologically acceptable salts thereof have a low toxicity and an outstanding vasodilatory action which manifests itself in a lowering of the blood pressure; furthermore, an inhibition of adrenergic β-receptors has also been observed.

By lower alkyl radicals in the substituents $R_1$, $R_2$, $R_4$, $R_5$, $R_6$, $R_7$, $R_8$ and $R_9$, there are to be understood straight-chained and branched radicals with up to 6 and preferably up to 4 carbon atoms, for example methyl, ethyl, isopropyl, n-propyl, n-butyl, isobutyl, tert.-butyl or n-hexyl radicals, methyl and ethyl radicals being especially preferred.

Hydroxyalkyl radicals of the substituents $R_1$, $R_2$, $R_6$ and $R_7$ contain up to 4 carbon atoms, the 2-hydroxyethyl and the hydroxymethyl radicals being preferred.

Alkoxy radicals of the substituents $R_4$, $R_5$, $R_8$ and Z contain up to 6 and preferably up to 4 carbon atoms, for example methoxy, ethoxy, propoxy, butoxy and pentoxy radicals, the methoxy and ethoxy radicals being preferred.

As alkoxycarbonyl radicals of the substituents $R_4$, $R_5$ and $R_8$, the methoxycarbonyl and ethoxycarbonyl radicals are especially preferred.

Alkylthio radicals of the substituents $R_4$, $R_5$ and $R_8$ contain up to 6 and preferably up to 4 carbon atoms, the methylthio radical being preferred.

Alkanoyl radicals of the substituents $R_8$ contain up to 8 and preferably up to 6 carbon atoms, the alkyl moiety being straight-chained, branched or cyclic, the acetyl and pivaloyl radicals being preferred.

By lower alkanoyloxyalkyl radicals of the substituents $R_1$ and $R_2$, there are to be understood those with up to 6 carbon atoms, the acetoxymethyl radical being preferred.

Aroyl radicals of the substituents $R_8$ are preferably benzoyl or naphthoyl radicals, which can preferably be substituted by halogen, methyl or methoxy.

According to the present invention, by halogen there is to be understood fluorine, chlorine, bromine or iodine, fluorine, chlorine and bromine being preferred.

The new compounds of general formula (I) can be prepared in known manner, for example:

(a) reacting a compound of the formula:

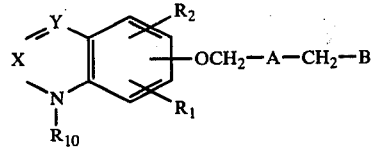

wherein X, Y, $R_1$ and $R_2$ have the same meanings as above, B is a reactive residue, A is a >$CH_2$, >C=O or >CH-E radical, E being an —O—$R_{10}$ radical or, together with B, representing an oxygen atom, and $R_{10}$ is a hydrogen atom or a protective group G, whereby, in the case of tautomerizable indazoles, the protective group G can also be on the second nitrogen atom X, with a compound of the general formula:

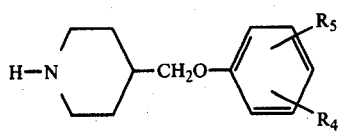

wherein $R_4$ and $R_5$ have the same meanings as above, and, when A is a >C=O group, the product obtained is subsequently reduced; or (b) reacting a compound of the general formula:

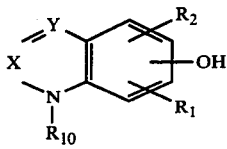

wherein X, Y, R$_1$, R$_2$ and R$_{10}$ have the same meanings as above, with a compound of the general formula:

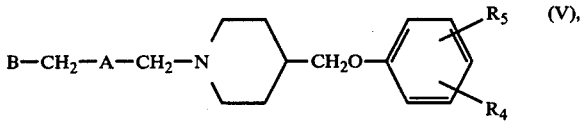

wherein A, B, R$_4$ and R$_5$ have the same meanings as above, and, when A is a >C=O group, the product obtained is subsequently reduced; or (c) reacting and cyclizing a compound of the general formula:

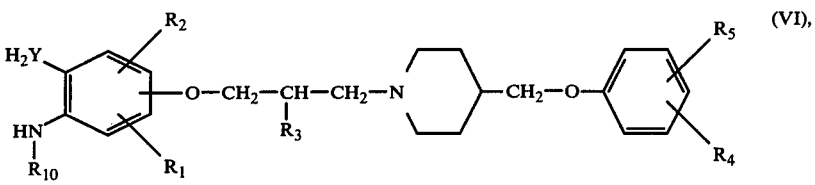

wherein R$_1$, R$_2$, R$_3$, R$_4$, R$_5$, R$_{10}$ and Y have the same meanings as above, with a compound of the general formula:

or with a reactive derivative thereof, wherein X has the same meaning as above; or (d) for the case in which X and Y in general formula (I) represent —CH=, reducing and cyclizing a compound of the general formula:

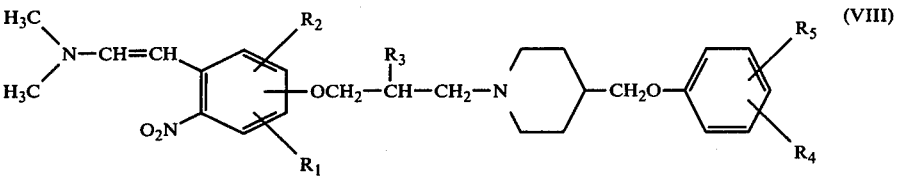

wherein R$_1$, R$_2$, R$_3$, R$_4$ and R$_5$ have the same meanings as above; and subsequently, when R$_8$ is to represent an alkanoyl radical or an optionally substituted aroyl radical, the hydroxyl group possibly present as R$_3$ is esterified or when R$_8$ is a hydrogen atom, the ester group possibly present as R$_3$ is hydrolyzed, and also a possibly present protective group G is split off or when one or more of the symbols R$_1$, R$_2$ and R$_9$ is to represent a hydroxymethyl radical, this is produced from an alkoxycarbonyl radical by reduction or from an alkanoyloxymethyl radical by hydrolysis or a methyl radical is produced by reducing a hydroxymethyl, acyloxymethyl or alkoxycarbonyl radical; and the compounds obtained are then, if desired, converted into pharmacologically acceptable salts.

Reactive residues B in compounds of general formulae (II) and (V) are, in particular, acid residues, for example of hydrohalic acids or sulphonic acids.

Compounds of general formula (II) in which X and Y represent

are known from Helv. Chim. Acta, 54, 2418/1971 and those in which X is a nitrogen atom and Y is

are described in U.S. Pat. application Ser. No. 790,648, filed Apr. 25, 1977, now pending. Compounds of general formula (III) are known from U.S. Pat. application Ser. No. 737,518, filed Nov. 1, 1976, now pending.

Insofar as these compounds have not previously actually been prepared, they can be prepared in a manner analogous to that described in the above-mentioned references.

Process a) and b) according to the present invention are preferably carried out in an organic solvent which is inert under the reaction conditions, for example, toluene, dioxan, ethylene glycol dimethyl ether, ethanol, n-butanol or dimethylformamide, optionally in the presence of an acid-binding agent.

The reaction of the compounds of general formula (IV) with the compounds of general formula (V) is preferably carried out in the presence of an acid acceptor, with the exclusion of oxygen. However, it is also possible to use alkali metal salts of the hydroxy compounds of general formula (IV).

Compounds of general formula (IV) are, when X and Y stand for —C(R$_9$)=, described in Helv. Chim. Acta, 54, 2411/1971, when X is a nitrogen atom and Y stands for —C(R$_9$)=, described in U.S. Pat. application Ser. No. 790,646, filed Apr. 25, 1977, now pending, when Y is a nitrogen atom and X stands for —C(R$_9$)= described in Helv. Chim. Acta, 35, 1740/1952 and when X and Y are nitrogen atoms described in J.C.S., 1956, 569.

When it is necessary to reduce a >C=O group, this can be carried out, for example, by means of a complex metal hydride, such as sodium borohydride, or by catalytic hydrogenation with the use of a noble metal catalyst.

As reactive derivatives of compounds of general formula (VII) in which X stands for —R$_9$C≡, it is preferred to use carboxylic acid esters, orthoesters, halides and amides and when X is a nitrogen atom, there is preferably used nitrous acid produced in situ from an inorganic nitrite and an aqueous mineral acid or, when working in an anhydrous medium, from a lower alkyl nitrous acid ester.

The reduction of the substituents R$_1$, R$_2$ and R$_9$ in compounds of general formula (I) which is possibly to be carried out can take place by means of a complex metal hydride, for example lithium aluminum hydride, or by catalytic hydrogenation in the presence of a noble metal catalyst or of Raney nickel.

The hydrolysis of the R$_1$, R$_2$ and R$_9$ groups in compounds of general formula (I) can be carried out in the usual manner under acidic or basic conditions.

The esterification of a hydroxyl group R$_3$ is carried out in the usual manner by reaction with an acid halide or acid anhydride, optionally in the presence of an acid-binding agent, for example pyridine.

The protective groups G can be lower alkanoyl radicals, for example acetyl radicals, aroyl radicals, for example benzoyl radicals, arylmethyl radicals, for example benzyl radicals, or cyclic ethers, for example the tetrahydropyranyl radical. Depending upon the nature of the protective group G, it can be split off in the usual manner hydrolytically or hydrogenolytically.

For the conversion of the compounds of general formula (I) into their pharmacologically acceptable salts, they are preferably reacted in an organic solvent with an inorganic or organic acid, for example hydrochloric acid, hydrobromic acid, phosphoric acid, sulphuric acid, acetic acid, citric acid, maleic acid or benzoic acid.

The compounds of general formula (I) according to the present invention can be obtained in the form of a racemic mixture. The separation of the racemate into the optically-active forms is carried out according to the usual methods via the diastereomeric salts. As active acids it is preferable to use tartaric acid, malic acid, campheric acid or camphor-sulphonic acid.

For the preparation of pharmaceuticals, the compounds of general formula (I) are mixed in the usual manner with appropriate pharmaceutical carrier substances, aroma, flavoring and coloring materials and formed, for example, into tablets or dragees, or, with the addition of appropriate adjuvants, suspended or dissolved in water or in an oil, for example olive oil.

The new compounds of general formula (I) according to the present invention can be administered enterally or parenterally in liquid or solid form. As injection medium, it is preferable to use water which contains the additives usual in the case of injection solutions, such as stabilizing agents, solubilizing agents or buffers. Additives of this type include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols); compositions which are suitable for oral administration can, if desired, contain flavoring and sweetening agents.

Apart from the compounds mentioned in the specific examples, the following compounds are, according to the present invention, also preferred:

4-[2-hydroxy-3-(4-phenoxymethylpiperidino)-propoxy]-6-tert.-butylindole;

4-[2-hydroxy-3-(4-phenoxymethylpiperidino)-propoxy]-6-methylbenzimidazole;

4-[2-hydroxy-3-(4-phenoxymethylpiperidino)-propoxy]-6-methylbenzotriazole; and

4-[2-hydroxy-3-(4-phenoxymethylpiperidino)-propoxy]-3-methylindazole.

The following examples are given for the purpose of illustrating the present invention:

EXAMPLE 1

4-[2-Hydroxy-3-(4-phenoxymethylpiperidino)-propoxy]-indole

A solution of 6.0 g. 4-(2,3-epoxypropoxy)-indole and 6.0 g. 4-phenoxymethylpiperidine in 50 ml. n-butanol is boiled for 4 to 6 hours. The solvent is subsequently evaporated off in a vacuum. The evaporation residue is taken up in about 300 to 400 ml. 0.5N acetic acid and the solution is shaken out with diethyl ether. The ethereal phase is discarded and the aqueous phase is rendered alkaline with an aqueous solution of potassium carbonate. The oil which precipitates out is extracted several times with diethyl ether/ethyl acetate (1:1 v/v). The organic phase is dried, treated with active charcoal and the solution then evaporated in a vacuum. The residue is dissolved in a mixture of 60 ml. diethyl ether and 25 ml. ethyl acetate and the solution mixed with 3.0 g. acetic acid. The mixture is left to crystallize overnight and then filtered off with suction. After recrystallization from isopropanol, there are obtained 8.0 g. (about 57% of theory) 4-[2-hydroxy-3-(4-phenoxymethylpiperidino)-propoxy]-indole in the form of the acetate; m.p. 127°–129° C.

The benzoate is prepared in the following manner: 7.3 g. 4-[2-hydroxy-3-(4-phenoxymethylpiperidino)-propoxy]-indole are dissolved in 25 ml. ethyl acetate. A solution of 2.3 g. benzoic acid in 25 ml. ethyl acetate is added thereto. The precipitate obtained is filtered off with suction and recrystallized from about 50 ml. isopropanol. There are obtained 4.4 g. 4-[2-hydroxy-3-(4-phenoxymethylpiperidino)-propoxy]-indole in the form of the benzoate; m.p. 146°–147° C.

When using 0.94 g. S-4-(2,3-epoxypropoxy)-indole and 0.95 g. 4-phenoxymethylpiperidine, there is obtained, by boiling under reflux in 50 ml. butanol, evaporation, taking up in ethyl acetate and mixing with 0.44 ml. acetic acid, 0.56 g. S(−)-4-[2-hydroxy-3-(4-phenoxymethylpiperidino)-propoxy]-indole in the form of the acetate (26% of theory); m.p. 121°–124° C.; $[\alpha]_D^{20} = -8.3°$ (1.5% solution in methanol).

EXAMPLE 2

The compounds set out in the following table are prepared in a manner analogous to that described in Example 1:

Table 1

| | | Yield % | m.p. °C (solvent) |
|---|---|---|---|
| a) | 4-[2-hydroxy-3-(4-phenoxymethyl-piperidino)-propoxy]-2-ethoxy-carbonylindole from 4-(2,3-epoxypropoxy)-2-ethoxy-carbonylindole and 4-phenoxy-methylpiperidine | 95 | 170 (isopropanol) |
| b) | 4-[2-hydroxy-3-(4-phenoxymethyl-piperidino)-propoxy]-2-carbamoyl-indole from 4-(2,3-epoxypropoxy)-2-carbamoyl-indole and 4-phenoxymethyl-piperidine | 59 | 182 (ethyl acetate) |
| c) | 4-[2-hydroxy-3-(4-phenoxymethyl-piperidino)-propoxy]-2-dimethyl-aminocarbonylindole from 4-(2,3-epoxypropoxy)-2-dimethyl-aminocarbonylindole and 4-phenoxy-methylpiperidine | 93 | 178 (isopropanol) |
| d) | 4-[2-hydroxy-3-(4-phenoxymethyl-piperidino)-propoxy]-6-methoxy-carbonylindole from 4-(2,3-epoxypropoxy)-6-methoxy-carbonylindole and 4-phenoxymethyl-piperidine | 87 | 139–140 (ethyl acetate) |
| e) | 4-[2-hydroxy-3-(4-phenoxymethyl-piperidino)-propoxy]-6-methyl-indole from 4-(2,3-epoxypropoxy)-6-methyl-indole and 4-phenoxymethyl-piperidine | 38 | 122–123 (ethyl acetate) |
| f) | 2-ethoxycarbonyl-4-[2-hydroxy-3-(4-phenoxymethylpiperidino)-propoxy]-6-methylindole benzoate from 2-ethoxycarbonyl-4-(2,3-epoxy-propoxy)-6-methylindole and 4-phenoxymethylpiperidine | 44 | 189 (isopropanol) |
| g) | 4-{2-hydroxy-3-[4-(2-chlorophenoxy-methyl)-piperidino]-propoxy}-indole benzoate from 4-(2,3-epoxypropoxy)-indole and 4-(2-chlorophenoxymethyl)-piperidine | 21 | 140–142 (ethyl acetate) |
| h) | 4-{2-hydroxy-3-[4-(3-chlorophenoxy-methyl)-piperidino]-propoxy}-indole benzoate from 4-(2,3-epoxypropoxy)-indole and 4-(3-chlorophenoxymethyl)-piperidine | 42 | 149–151 (ethyl acetate) |
| i) | 4-{2-hydroxy-3-[4-(4-chlorophenoxy-methyl)-piperidino]-propoxy}-indole benzoate from 4-(2,3-epoxypropoxy)-indole and 4-(4-chlorophenoxymethyl)-piperidine | 36 | 156–158 (ethyl acetate) |
| j) | 4-{2-hydroxy-3-[4-(2-methoxyphenoxy-methyl)-piperidino]-propoxy}-indole benzoate from 4-(2,3-epoxypropoxy)-indole and 4-(2-methoxyphenoxymethyl)-piperidine | 37 | 115–117 (ethyl acetate) |
| k) | 4-{2-hydroxy-3-[4-(2-methylphenoxy-methyl)-piperidino]-propoxy}-indole benzoate from 4-(2,3-epoxypropoxy)-indole and 4-(2-methylphenoxymethyl)-piperidine | 39 | 128–129 (ethyl acetate) |
| l) | 4-{2-hydroxy-3-[4-(3-methylphenoxy-methyl)-piperidino]-propoxy}-indole benzoate from 4-(2,3-epoxypropoxy)-indole and 4-(3-methylphenoxymethyl)-piperidine | 39 | 152–154 (ethyl acetate) |
| m) | 4-{2-hydroxy-3-[4-(2-methylthio-phenoxymethyl)-piperidino]-propoxy}-indole from 4-(2,3-epoxypropoxy)-indole and 4-(2-methylthiophenoxymethyl)-piperidine | 40 | 108–110 (ethyl acetate) |
| n) | 4-{2-hydroxy-3-[4-(4-fluorophenoxy-methyl)-piperidino]-propoxy}-6-methylindole from 4-(2,3-epoxypropoxy)-6-methylindole and 4-(4-fluorophenoxymethyl)-piperidine | 20 | 137–139 (ethyl acetate) |
| o) | 4-{2-hydroxy-3-[4-(3-methylphenoxy- | 31 | 138–140 |

Table 1-continued

| | | Yield % | m.p. °C. (solvent) |
|---|---|---|---|
| | methyl)-piperidino]-propoxy}-6-methylindole benzoate from 4-(2,3-epoxypropoxy)-6-methylindole and 4-(3-methylphenoxymethyl)-piperidine | | (ethyl acetate) |
| p) | 4-{2-hydroxy-3-[4-(2-benzyloxy-phenoxymethyl)-piperidino]-propoxy}-indole from 4-(2,3-epoxypropoxy)-indole and 4-(2-benzyloxyphenoxymethyl)-piperidine | 90 | oil |
| q) | 4-{2-hydroxy-3-[4-(4-benzyloxy-phenoxymethyl)-piperidino]-propoxy}-indole from 4-(2,3-epoxypropoxy)-indole and 4-(4-benzyloxyphenoxymethyl)-piperidine | 71 | 113 (diethyl ether) |
| r) | 4-[2-hydroxy-3-(4-phenoxymethyl-piperidino)-propoxy]-2-pivaloyloxy-methylindole from 4-(2,3-epoxypropoxy)-2-pivaloyloxy-methylindole and 4-(phenoxymethyl)-piperidine | 22 | 130–132 (ethyl acetate) |
| s) | 4-{2-hydroxy-3-[4-(2-methoxyphenoxy-methyl)-piperidino]-propoxy}-2-methyl-indole from 4-(2,3-epoxypropoxy)-2-methylindole and 4-(2-methoxyphenoxymethyl)-piperidine | 38 | 137–138 (ethylacetate) |
| t) | 4-{2-hydroxy-3-[4-(2-chlorophenoxy-methyl)-piperidino]-propoxy}-2-methyl-indole from 4-(2,3-epoxypropoxy)-2-methylindole and 4-(2-chlorophenoxymethyl)-piperidine | | |
| u) | 4-{2-hydroxy-3-[4-(2,5-dimethyl-phenoxymethyl)-piperidino]-propoxy}-indole from 4-(2,3-epoxypropoxy)-indole and 4-(2,5-dimethylphenoxymethyl)-piperidine | 44 | 153–155 (ethyl acetate) |
| v) | 5-[2-hydroxy-3-(4-phenoxymethyl-piperidino)-propoxy]-indole from 5-(2,3-epoxypropoxy)-indole and 4-phenoxymethylpiperidine | 59 | 121–123 (ethanol) |
| w) | 6-[2-hydroxy-3-(4-phenoxymethyl-piperidino)-propoxy]-indole from 6-(2,3-epoxypropoxy)-indole and 4-phenoxymethylpiperidine | 46 | 144–145 (ethanol) |

EXAMPLE 3

4-[3-(4-Phenoxymethylpiperidino)-propoxy]-indole

A mixture of 4.0 g. 4-(3-bromopropoxy)-indole, 3.4 g. 4-phenoxymethylpiperidine, 50 ml. isopropanol and 2.4 g. N-ethyldiisopropylamine is heated under reflux for 6 hours. The reaction mixture is then evaporated and the evaporation residue is taken up in chloroform and washed with a dilute aqueous solution of sodium hydroxide and then with water. After evaporation of the organic phase, the evaporation residue is recrystallized from ethyl acetate. There are obtained 2.0 g. (34% of theory) 4-[3-(4-phenoxymethylpiperidino)-propoxy]-indole; m.p. 118°–119° C.

EXAMPLE 4

The compounds set out in the following table are prepared in a manner analogous to that described in Example 3:

Table 2

| | | Yield % | m.p. °C. (solvent) |
|---|---|---|---|
| a) | 5-[3-(4-phenoxymethylpiperidino)-propoxy]-indole | 47 | 107–108 (ethyl |

Table 2-continued

| | | Yield % | m.p. °C. (solvent) |
|---|---|---|---|
| | from 5-(3-chloropropoxy)-indole and 4-phenoxymethylpiperidine | | acetate) |
| b) | 6-[3-(4-phenoxymethylpiperidino)-propoxy]-indole from 6-(3-chloropropoxy)-indole and 4-phenoxymethylpiperidine | 36 | 123–124 (isopropanol) |

EXAMPLE 5

4-[2-Hydroxy-3-(4-phenoxymethylpiperidino)-propoxy-2-ethoxycarbonylindole

A mixture of 0.9 g. 2-ethoxycarbonyl-4-hydroxyindole, 1.7 g. N-(2,3-epoxypropyl)-4-phenoxymethylpiperidine, 1.2 g. potassium carbonate and 50 ml. acetonitrile is heated under reflux for 10 hours. The reaction mixture is then filtered while still hot and the filtrate left to cool overnight. 0.3 g. (15% of theory) 4-[2-hydroxy-3-(4-phenoxymethylpiperidino)-propoxy]-2-ethoxycarbonylindole crystallize out; m.p. 168°–170° C.

EXAMPLE 6

4-[2-Hydroxy-3-(4-phenoxymethylpiperidino)-propoxy]-2-hydroxymethylindole

To a suspension of 0.95 g. lithium aluminum hydride in 45 ml. anhydrous tetrahydrofuran, there is added dropwise at 0° C. a solution of 4.5 g. 4-[2-hydroxy-3-(4-phenoxymethylpiperidino)-propoxy]-2-ethoxycarbonylindole in 25 ml. anhydrous tetrahydrofuran. The reaction mixture is stirred for 1 hour at ambient temperature, then decomposed with an aqueous solution of sodium chloride, while cooling, filtered, then washed with tetrahydrofuran and the combined filtrates mixed with 0.01 mol benzoic acid. The benzoate thus obtained is recrystallized from 25 ml. ethyl acetate to give 2.5 g. 4-[2-hydroxy-3-(4-phenoxymethylpiperidino)-propoxy]-2-hydroxymethylindole benzoate (47% of theory); m.p. 145°–146° C.

EXAMPLE 7

The compounds set out in the following table are obtained in a manner analogous to that described in Example 6:

Table 3

| | | Yield % | m.p. ° C. (solvent) |
|---|---|---|---|
| a) | 4-[2-hydroxy-3-(4-phenoxymethyl-piperidino)-propoxy]-6-hydroxy-methylindole benzoate from 4-[2-hydroxy-3-(4-phenoxymethyl-piperidino)-propoxy]-6-methoxy-carbonylindole | 17 | 153–155 (ethyl acetate) |
| b) | 4-[2-hydroxy-3-(4-phenoxymethyl-piperidino)-propoxy]-6-hydroxy-methyl-5-methylindole from 4-[2-hydroxy-3-(4-phenoxymethyl-piperidino)-propoxy]-6-methoxy-carbonyl-5-methylindole | | |

EXAMPLE 8

4-[2-Hydroxy-3-(4-phenoxymethylpiperidino)-propoxy]-indole 2-carboxylic acid To a suspension of 2.0 g. 4-[2-hydroxy-3-(4-phenoxymethylpiperidino)-propoxy]-2-ethoxycarbonylindole in 50 ml. dioxane, there is added a solution of 0.5 g. potassium hydroxide in 25 ml. water. The reaction mixture is stirred for 16 hours at 50° C., then evaporated and the evaporation residue taken up in water and neutralized with dilute sulphuric acid. There are obtained 1.8 g. (96% of theory) 4-[2-hydroxy-3-(4-phenoxymethylpiperidino)-propoxy]-indole-2-carboxylic acid; m.p. 218°–220° C. (decomp.).

EXAMPLE 9

4-[2-Hydroxy-3-(4-phenoxymethylpiperidino)-propoxy]-2-methylindole

A mixture of 5.9 g. 4-[2-hydroxy-3-(4-phenoxymethylpiperidino)-propoxy]-2-hydroxymethylindole, 114 ml. acetic anhydride and 55 ml. pyridine is stirred for 4 hours at ambient temperature and then evaporated in a vacuum. The evaporation residue is taken up in ethyl acetate, washed with water and evaporated. The diacetyl compound (8.0 g.) thus obtained is dissolved in 100 ml. methanol and hydrogenated in the presence of 2.0 g. 10% palladium-charcoal at a hydrogen pressure of 1 bar.

After the take up of the calculated amount of hydrogen, the reaction mixture is filtered and concentrated to half its volume. The pH value is then adjusted to 9 with a 2N solution of sodium methanolate in methanol and heated under reflux for 10 minutes. The reaction mixture is then poured into water and extracted with chloroform. After evaporation of the extract, the residue is taken up in ethyl acetate, 0.01 mol benzoic acid added thereto and the benzoate thus obtained recrystallized from 25 ml. isopropanol. There is obtained 1.6 g. (29% of theory) 4-[2-hydroxy-3-(4-phenoxymethylpiperidino)-propoxy]-2-methylindole benzoate; m.p. 145°–148° C.

EXAMPLE 10

The compounds set out in the following table are prepared in a manner analogous to that described in Example 9:

Table 4

| | | Yield % | m.p. ° C. (solvent) |
|---|---|---|---|
| a) | 4-[2-hydroxy-3-(4-phenoxymethyl-piperidino)-propoxy]-6-methyl-indole from 4-[2-hydroxy-3-(4-phenoxymethyl-piperidino)-propoxy]-6-hydroxy-methylindole | 23 | 122–123 (ethyl acetate) |
| b) | 4-[2-hydroxy-3-(4-phenoxymethyl-piperidino)-propoxy]-5,6-dimethyl-indole from 4-[2-hydroxy-3-(4-phenoxymethyl-piperidino)-propoxy]-6-hydroxy-methyl-5-methylindole | | |

EXAMPLE 11

4-[2-Pivaloyloxy-3-(4-phenoxymethylpiperidino)-propoxy]-indole.

A mixture of 4.4 g. 4-[2-hydroxy-3-(4-phenoxymethylpiperidino)-propoxy]-indole acetate, 10.2 g. pivalic acid and 2.0 g. pivalic anhydride is stirred until a solution is obtained and then left to stand for 2 days at ambient temperature. The reaction mixture is then poured on to ice, the pH value adjusted to 9 with an aqueous solution of ammonia, extracted with methylene chloride, the extract evaporated and the evaporation residue triturated with diethyl ether. There are obtained 3.2 g. (69% of theory) 4-[2-pivaloyloxy-3-(4-phenoxymethylpiperidino)-propoxy]-indole; m.p. 103°–105° C.

EXAMPLE 12

In a manner analogous to that described in Example 11, there are prepared the compounds set out in the following table:

Table 5

| | | Yield % | m.p. ° C. (solvent) |
|---|---|---|---|
| a) | 4-{2-pivaloyloxy-3-[4-(2-methoxy-phenoxymethyl)-piperidino]-propoxy}-indole from 4-{2-hydroxy-3-[4-(2-methoxyphenoxy-methyl)-piperidino]-propoxy}-indole and pivalic anhydride | 66 | 107 (diethyl ether) |
| b) | 4-[2-pivaloyloxy-3-(4-phenoxymethyl-piperidino)-propoxy]-6-methylindole from 4-[2-hydroxy-3-(4-phenoxymethyl-piperidino)-propoxy]-6-methylindole and pivalic anhydride | 70 | 81 (ligroin/ ether) |
| c) | 4-[2-pivaloyloxy-3-(4-phenoxymethyl-piperidino)-propoxy]-6-pivaloyloxy- | 23 | 76–78 (heptane/ |

Table 5-continued

| | | Yield % | m.p. °C. (solvent) |
|---|---|---|---|
| | methylindole from 4-[2-hydroxy-3-(4-phenoxymethyl-piperidino)-propoxy]-6-hydroxymethyl-indole and pivaloyl chloride | | ether) |
| d) | 4-[2-benzoyloxy-3-(4-phenoxymethyl-piperdino)-propoxy]-indole from 4-[2-hydroxy-3-(4-phenoxymethyl-piperidino)-propoxy]-indole and benzoic anhydride | 40 | 108–110 (diethyl ether) |
| e) | 4-[2-pivaloyloxy-3-(4-phenoxymethyl-piperidino)-propoxy]-2-pivaloyloxy-methylindole from 4-[2-hydroxy-3-(4-phenoxymethyl-piperidino)-propoxy]-2-pivaloyloxy-methylindole and pivalic anhydride | 24 | 93–95 (heptane/ether) |
| f) | 4-{2-pivaloyloxy-3-[4-(2-methyl-phenoxymethyl)-piperidino]-propoxy}-2-methylindole from 4-{2-hydroxy-3-[4-(2-methylphenoxy-methyl)-piperidino]-propoxy-2-methyl indole and pivalic anhydride | | |

EXAMPLE 13

4-{2-Hydroxy-3-[4-(2-hydroxyphenoxymethyl)-piperidino]-propoxy}-indole 13.8 g. 4-{2-Hydroxy-3-[4-(2-benzyloxyphenoxymethyl)piperidino]-propoxy}-indole in 250 ml. methanol are hydrogenated at ambient temperature and at a hydrogen pressure of 1 bar in the presence of 3 g. 5% palladium-charcoal. The reaction mixture is then filtered, the filtrate is evaporated and the evaporation residue is recrystallized from ethyl acetate. There are obtained 4.7 g. (42% of theory) 4-{2-hydroxy-3-[4-(2-hydroxyphenoxymethyl)-piperidino]-propoxy}-indole; m.p. 119°–121° C.

EXAMPLE 14

In a manner analogous to that described in Example 13, there are prepared the compounds set out in the following table:

Table 6

| | | Yield % | m.p. °C. (solvent) |
|---|---|---|---|
| a) | 4-{2-hydroxy-3-[4-(4-hydroxyphenoxymethyl)-piperidino]-propoxy}-indole from 4-{2-hydroxy-3-[4-(4-benzyloxyphenoxymethyl)-piperidino]-propoxy}-indole | 39 | 167 (isopropanol) |
| b) | 4-{2-hydroxy-3-[4-(2-carboxyphenoxymethyl)-piperidino]-propoxy}-indole from 4-{2-hydroxy-3-[4-(2-benzyloxycarbonylphenoxymethyl)-piperidino]-propoxy}-indole | | |

EXAMPLE 15

4-[3-(4-Phenoxymethylpiperidine)-propoxy]-benzimidazole

A mixture of 7.0 g. 2,3-diamino-1-[3-(4-phenoxymethylpiperidino)-propoxy]-benzene trihydrochloride and 100 ml. formic acid is heated under reflux for 2 days. The reaction mixture is then evaporated in a vacuum and the evaporation residue recrystallized from ethanol. There are obtained 3.34 g. (50% of theory) 4-[3-(4-phenoxymethylpiperidino)-propoxy]-benzimidazole dihydrochloride; m.p. 144°–146° C.

The 2,3-diamino-1-[3-(4-phenoxymethylpiperidino)-propoxy]-benzene trihydrochloride used as starting material can be prepared in the following manner:

1-(2-Amino-3-nitrophenoxy)-3-chloropropane

A mixture of 21.0 g. 2-amino-3-nitrophenol, 20.1 g. potassium carbonate and 750 ml. butanone is heated under reflux for 1 hour, mixed with 64.0 g. 1-bromo-3-chloropropane, further heated under reflux for 3 hours, filtered and the filtrate evaporated. There are obtained 29.0 g. 1-(2-amino-3-nitrophenoxy)-3-chloropropane (99% of theory) in the form of an amorphous substance.

2-Amino-3-nitro-1-[3-(4-phenoxymethylpiperidino)-propoxy]-benzene hydrochloride

A mixture of 17.5 g. 1-(2-amino-3-nitrophenoxy)-3-chloropropane, 31.0 g. 4-phenoxymethylpiperidine and 500 ml. ethanol is heated under reflux for 7 days. After subsequent evaporation of the reaction mixture, the evaporation residue is extracted with 500 ml. diethyl ether and the extract is acidified with dilute hydrochloric acid and evaporated. There are obtained 29.7 g. (86% of theory) 2-amino-3-nitro-1-[3-(4-phenoxymethylpiperidino)-propoxy]-benzene hydrochloride in the form of an amorphous salt.

2,3-Diamino-1-[3-(4-phenoxymethylpiperidino)-propoxy]-benzene trihydrochloride

A solution of 28.0 g. 2-amino-3-nitro-1-[3-(4-phenoxymethylpiperidino)-propoxy]-benzene hydrochloride in 600 ml. ethanol and 200 ml. water is hydrogenated at ambient temperature and atmospheric pressure in the presence of 0.4 g. platinum oxide. After filtration, the filtrate obtained is acidified with dilute hydrochloric acid, evaporated and the evaporation residue dissolved in ethanol/ethyl acetate. There are obtained 21.4 g. (70% of theory) 2,3-diamino-1-[3-(4-phenoxymethylpiperidino)-propoxy]-benzene trichloride in the form of an amorphous salt.

EXAMPLE 16

The compounds set out in the following table are prepared in a manner analogous to that described in Example 15:

Table 7

| | | Yield % | m.p. °C. (solvent) |
|---|---|---|---|
| a) | 4-[2-hydroxy-3-(4-phenoxymethyl-piperidino)-propoxy]-benzimidazole dihydrochloride from 2,3-diamino-1-[2-hydroxy-3-(4-phenoxymethylpiperidino)-propoxy]-benzene trihydrochloride and formic acid | 47 | 123–125 (ethanol) |
| b) | 4-{2-hydroxy-3-[4-(2-methoxyphenoxymethyl)-piperidino]-propoxy}-benzimidazole dihydrochloride from 2,3-diamino-1-{2-hydroxy-3-[4-(2-methoxyphenoxymethyl)-piperidino]-propoxy}-benzene trihydrochloride and formic acid | 39 | 144–145 (ethanol) |
| c) | 4-{2-hydroxy-3-[4-(3-methylphenoxymethyl)-piperidino]-propoxy}-benzimidazole dihydrochloride from 2,3-diamino-1-{2-hydroxy-3-[4-(3-methylphenoxymethyl)-piperidino]-propoxy}-benzene trihydrochloride and formic acid | 22 | 118–120 (ethanol) |
| d) | 4-{2-hydroxy-3-[4-(2-chlorophenoxymethyl)-piperidino]-propoxy}-benzimidazole dihydrochloride from 2,3-diamino-1-{2-hydroxy-3-[4-(2- | 39 | 140–142 (ethanol) |

Table 7-continued

| | | Yield % | m.p. ° C. (solvent) |
|---|---|---|---|
| | chlorophenoxymethyl)-piperidino]-propoxy}-benzene trihydrochloride and formic acid | | |
| e) | 4-[2-hydroxy-3-(4-phenoxymethyl-piperidino)-propoxy]-6-methyl-benzimidazole dihydrochloride from 2,3-diamino-1-[2-hydroxy-3-(4-phenoxymethylpiperidino)-propoxy]-5-methyl-benzene trihydrochloride and formic acid | | |

The 2,3-diamino-1-[2-hydroxy-3-(4-phenoxymethyl-piperidino)-propoxy]-benzene trihydrochloride used as starting material can be prepared as follows:

A mixture of 40.0 g. 1-(2-amino-3-nitrophenoxy)-2,3-epoxypropane, 36.2 g. 4-phenoxymethylpiperidine and 450 ml. ethanol is stirred for 18 hours at ambient temperature and the solution thereby obtained of 2-amino-1-[2-hydroxy-3-(4-phenoxymethylpiperidino)-propoxy]-3-nitrobenzene (m.p. 117°–118° C.) is subsequently hydrogenated at ambient temperature in the presence of 1.0 g. platinum oxide. After filtration, the filtrate obtained is acidified with dilute hydrochloric acid, evaporated and the evaporation residue redissolved in ethanol/ethyl acetate. There are obtained 72.3 g. 2,3-diamino-1-[2-hydroxy-3-(4-phenoxymethylpiperidino)-propoxy]-benzene trihydrochloride (81% of theory) in the form of an amorphous substance.

1-(2-Amino-3-nitrophenoxy)-2,3-epoxypropane is a known compound.

The other intermediates mentioned above in Example 16 can be prepared in a corresponding manner.

EXAMPLE 17

4-[2-Pivaloyloxy-3-(4-phenoxymethylpiperidino)-propoxy]-benzimidazole 3.8 g. 4-[2-Hydroxy-3-(4-phenoxymethylpiperidino)-propoxy]-benzimidazole and 1.3 g. pivaloyl chloride are boiled under reflux for 2 hours in 25 ml. pyridine. After stripping off the solvent, the residue is taken up in 100 ml. chloroform. The chloroform solution is thoroughly washed with water, dried over anhydrous sodium sulphate and finally mixed with 50 ml. ethereal hydrochloric acid. After evaporation and recrystallization from ethanol, there is obtained 4-[2-pivaloyloxy-3-(4-phenoxymethylpiperidino)-propoxy]-benzimidazole hydrochloride; m.p. 132°–134° C.

EXAMPLE 18

In a manner analogous to that described in Example 17, there can be prepared the following compound: 4-[2-(3,4,5-trimethoxybenzoyloxy)-3-(4-(2-chloro-phenoxymethyl)-piperidino)-propoxy]-benzimidazole from 4-[2-hydroxy-3-(4-(2-chloro-phenoxymethyl)-piperidino)-propoxy]-benzimidazole and 3,4,5-trimethoxybenzoyl chloride; yield 32% of theory; m.p. 158°–160° C.

EXAMPLE 19

4-[2-Hydroxy-3-(4-phenoxymethylpiperidino)-propoxy]-benzotriazole

To a suspension of 23.0 g. 2,3-diamino-1-[2-hydroxy-3-(4-phenoxymethylpiperidino)-propoxy]-benzene trihydrochloride in 150 ml. water and 8.8 ml. concentrated hydrochloric acid, there is added dropwise at 0° C. a solution of 3.3 g. sodium nitrite in 37 ml. water. After standing overnight, the reaction mixture is filtered and the precipitate is recrystallized from methanol. There are obtained 9.5 g. (47% of theory) 4-[2-hydroxy-3-(4-phenoxymethylpiperidino)-propoxy]-benzotriazole hydrochloride; m.p. 187°–189° C.

EXAMPLE 20

The compounds set out in the following table are prepared in a manner analogous to that described in Example 19:

Table 8

| | | Yield % | m.p. ° C. (solvent) |
|---|---|---|---|
| a) | 4-{2-hydroxy-3-[4-(2-methoxyphenoxy-methyl)-piperidino]-propoxy}-benzo-triazole hydrochloride from 2,3-diamino-1-{2-hydroxy-3-[4-(2-methoxyphenoxymethyl)-piperidino]-propoxy}-benzene trihydrochloride and sodium nitrite | 33 | 161–162 |
| b) | 4-{2-hydroxy-3-[4-(3-methylphenoxy-methyl)-piperidino]-propoxy}-benzo-triazole hydrochloride from 2,3-diamino-1-{2-hydroxy-3-[4-(3-methylphenoxymethyl)-piperidino]-propoxy}-benzene trihydrochloride and sodium nitrite | 37 | 206–208 |
| c) | 4-[3-(4-phenoxymethylpiperidino)-propoxy]-benzotriazole hydrochloride from 2,3-diamino-1-[3-(4-phenoxymethyl-piperidino)-propoxy]-benzene tri-hydrochloride and sodium nitrite | 56 | 259–260 |

EXAMPLE 21

4-[2-Pivaloyloxy-3-(4-phenoxymethylpiperidino)-propoxy]-benzotriazole

A mixture of 5.1 g. 4-[2-hydroxy-3-(4-phenoxyme-thylpiperidino)-propoxy]-benzotriazole hydrochloride, 6.7 g. pivalic anhydride and 33.3 g. molten pivalic acid is stirred for 3 days at ambient temperature, then poured on to ice, neutralized with an aqueous solution of ammonia and extracted with methylene chloride. After evaporation of the extract, the oily residue obtained is taken up in methanol and rendered weakly acidic with dilute hydrochloric acid. Upon evaporating the solvent, there are obtained 2.53 g. (38% of theory) 4-[2-pivaloyloxy-3-(4-phenoxymethylpiperidino)-propoxy]-benzotriazole hydrochloride; m.p. 131°–133° C.

EXAMPLE 22

In a manner analogous to that described in Example 21, there can be prepared the compounds set out in the following table:

Table 9

| | |
|---|---|
| a) | 4-{2-(4-methylbenzoyloxy)-3-[4-(2-methoxyphenoxymethyl)-piperidino]-propoxy}-benzotriazole from 4-{2-hydroxy-3-[4-(2-methoxy-phenoxymethyl)-piperidino]-propxy}-benzotriazole and 4-methylbenzoic anhydride in dioxan |
| b) | 4-{2-(2-chlorobenzoyloxy)-3-[4-(3-methylphenoxymethyl)-piperidino]-propxoy}-benzotriazole from 4-(2-hydroxy-3-[4-(3-methylphenoxy-methyl)-piperidino]-propoxy}-benzo-triazole and 2-chlorobenzene anhydride in dioxan |

EXAMPLE 23

4-[2-Hydroxy-3-(4-phenoxymethylpiperidino)-propoxy]-indazole

A mixture of 5.6 g. 4-(2,3-epoxypropoxy)-indazole, 11.2 g. 4-phenoxymethylpiperidine and 11 ml. dimethoxyethane is heated to 50° C. for 20 hours, mixed with 40 ml. diethyl ether, filtered and the precipitate obtained recrystallized from isopropanol. There are obtained 4.6 g. (41% of theory) 4-[2-hydroxy-3-(4-phenoxymethylpiperidino)-propoxy]-indazole; m.p. 142°–143° C.

Reaction of this indazole base with ethereal hydrochloric acid gives a hydrochloride which has a melting point of 220°–222° C.

EXAMPLE 24

The compounds set out in the following table can be prepared in a manner analogous to that described in Example 23:

Table 10

| | Yield % | m.p. ° C. (solvent) |
|---|---|---|
| a) 4-{2-hydroxy-3-[4-(2-chlorophenoxymethyl)-piperidino]-propoxy}-indazole from 4-(2,3-epoxypropoxy)-indazole and 4-(2-chlorophenoxymethyl)-piperidine | 43 | 154 (isopropanol) |
| b) 4-{2-hydroxy-3-[2-methylphenoxymethyl)-piperidino]-propoxy}-indazole from 4-(2,3-epoxypropoxy)-indazole and 4-(2-methylphenoxymethyl)-piperidine | 38 | 127–129 (isopropanol) |
| c) 4-{2-hydroxy-3-[4-(3-methylphenoxymethyl)-piperidino]-propoxy}-indazole from 4-(2,3-epoxypropoxy)-indazole and 4-(3-methylphenoxymethyl)-piperidine | 46 | 158–159 (isopropanol) |
| d) 4-{2-hydroxy-3-[4-(2-methoxyphenoxymethyl)-piperidino]-propoxy}-indazole from 4-(2,3-epoxypropoxy)-indazole and 4-(2-methoxyphenoxymethyl)-piperidine | 54 | 151–153 (isopropanol) |
| e) 4-[2-hydroxy-3-(4-phenoxymethylpiperidino)-propoxy]-5-methylindazole from 4-(2,3-epoxypropoxy)-5-methylindazole and 4-phenoxymethylpiperidine | 53 | 156–157 (isopropanol) |
| f) 4-[2-hydroxy-3-(4-phenoxymethylpiperidino)-propoxy]-6-methylindazole from 4-(2,3-epoxypropoxy)-6-methylindazole and 4-phenoxymethylpiperidine | 54 | 152–153 (isopropanol) |

EXAMPLE 25

4-[2-Hydroxy-3-(4-phenoxymethylpiperidino)-propoxy]-indazole 36.8 g. 1-Acetyl-4-(2,3-epoxypropoxy)-indazole are introduced at 80° C., into 127 g. 4-phenoxymethylpiperidine, stirred for 2 hours, 400 ml. diethyl ether added thereto and the precipitate obtained filtered off and recrystallized from isopropanol. There are obtained 34.3 g. (57% of theory) 4-[2-hydroxy-3-(4-phenoxymethylpiperidino)-propoxy]-indazole; m.p. 141°–142° C.

EXAMPLE 26

3-Acetoxymethyl-4-[2-hydroxy-3-(4-phenoxymethylpiperidino)-propoxy]-indazole hydrochloride A mixture of 4.7 g. 3-acetoxymethyl-4-(2,3-epoxypropoxy)-indazole, 3.8 g. 4-phenoxymethylpiperidine and 35 ml. 1,2-dimethoxyethane is heated to 50° C. for 20 hours. The reaction mixture is then evaporated in a vacuum, the evaporation residue is taken up in diethyl ether and the hydrochloride of the product formed is precipitated out by the addition of ethanolic hydrochloric acid. There are obtained 2.6 g. (30% of theory) 3-acetoxymethyl-4-[2-hydroxy-3-(4-phenoxymethylpiperidino)-propoxy]-indazole hydrochloride; m.p. 203°–204° C. (recrystallized from ethanol).

The 3-acetoxymethyl-4-(2,3-epoxypropoxy)-indazole used as starting material can be prepared as follows:

2-(2-Hydroxyethyl)-3-nitrophenyl benzyl ether

This is obtained, by the reaction of 2-methyl-3-nitrophenyl benzyl ether with paraformaldehyde and potassium tert.-butylate in dimethyl formamide, in the form of a yellow oil.

2-(2-Hydroxyethyl)-3-aminophenyl benzyl ether

This is obtained, by the reduction of 2-(2-hydroxyethyl)-3-nitrophenyl benzyl ether with hydrazine hydrate and Raney nickel in methanol, in the form of a greenish oil.

2-(2-Acetoxyethyl)-3-acetamidophenyl benzyl ether

This is obtained, by acetylating 2-(2-hydroxyethyl)-3-aminophenyl benzyl ether with acetic anhydride in toluene, in the form of colorless crystals; m.p. 118°–119° C.

1-Acetyl-3-acetoxymethyl-4-benzyloxy-indazole

This is obtained by nitrosation and subsequent ring closure by treating 2-(2-acetoxyethyl)-3-acetamidophenyl benzyl ether with isoamyl nitrite, sodium acetate and acetic anhydride in toluene at 80° C. It is obtained in the form of colorless crystals; m.p. 99°–100° C.

1-Acetyl-3-acetoxymethyl-4-hydroxyindazole

This is obtained by the hydrogenolysis of 1-acetyl-3-acetoxymethyl-4-benzyloxyindazole in tetrahydrofuran in the presence of 10% palladium charcoal, in the form of colorless crystals; m.p. 178°–179° C.

1-Acetyl-3-acetoxymethyl-4-(2,3-epoxypropoxy)-indazole

This is obtained, by the reaction of 1-acetyl-3-acetoxymethyl-4-hydroxyindazole with epibromohydrin and potassium carbonate in dimethylformamide at 60° C., in the form of colorless crystals; m.p. 127°–129° C.

3-Acetoxymethyl-4-(2,3-epoxypropoxy)-indazole

This is obtained by the partial aminolysis of 1-acetyl-3-acetoxymethyl-4-(2,3-epoxypropoxy)-indazole in liquid ammonia over the course of 5 hours; m.p. 119°–120° C.

EXAMPLE 27

4-[2-Hydroxy-3-(4-phenoxymethylpiperidino)-propoxy]-3-hydroxymethylindazole dihydrochloride Excess ethanolic hydrochloric acid is allowed to act upon 3-acetoxymethyl-4-[2-hydroxy-3-(4-phenoxymethylpiperidino)-propoxy]-indazole, followed by precipitation with diethyl ether and recrystallization of the precipitate from ethanol. There is obtained, in a yield of 48% of theory, 4-[2-hydroxy-3-(4-phenoxymethylpiperidino)-propoxy]-3-hydroxymethylindazole dihydrochloride in the form of pale yellow crystals; m.p. 183° C. (decomp.).

EXAMPLE 28

4-[2-Hydroxy-3-(4-phenoxymethylpiperidino)-propoxy]-7-methylindazole

A mixture of 4.0 g. 4-(2,3-epoxypropoxy)-2-benzyl-7-methylindazole, 2.4 g. 4-phenoxymethylpiperidine and 10 ml. 1,2-dimethoxyethane is heated to 60° C. for 20 hours. The reaction mixture is then evaporated and the evaporation residue is taken up in 150 ml. methanol and hydrogenated in the presence of 1 g. 10% palladium charcoal and in the presence of 20 ml. concentrated hydrochloric acid. After filtration, the filtrate is evaporated and the evaporation residue is taken up in a dilute aqueous solution of sodium hydroxide, extracted with methylene chloride and evaporated. There are obtained 3.9 g. (73% of theory) 4-[2-hydroxy-3-(4-phenoxymethylpiperidino)-propoxy]-7-methylindazole; m.p. 132°–135° C. (after recrystallization from isopropanol).

The 4-(2,3-epoxypropoxy)-2-benzyl-7-methylindazole used as starting material can be prepared as follows:

2,4-Dimethyl-3-nitrophenyl benzyl ether

This compound is obtained, by the reaction of 2,4-dimethyl-3-nitrophenol with benzyl chloride in the presence of potassium carbonate in dimethylformamide at 80° C., in the form of pale yellow leaflets; m.p. 65°–67° C.

3-Amino-2,4-dimethylphenyl benzyl ether

This is obtained, by the reduction of 2,4-dimethyl-3-nitrophenyl benzyl ether with hydrazine and Raney nickel in methanol, in the form of a dark oil.

3-Acetamido-2,4-dimethylphenyl benzyl ether

This is obtained by the acetylation of 3-amino-2,4-dimethylphenyl benzyl ether with acetic anhydride in toluene, in the form of colorless crystals; m.p. 160°–162° C.

4-Benzyloxy-7-methylindazole

This is obtained by the nitrosation and subsequent ring closure of 3-acetamido-2,4-dimethylphenyl benzyl ether by the action of isoamyl nitrite, sodium acetate and acetic anhydride in toluene at 80°–90° C. and subsequent aminolysis with isopropylamine, in the form of needles; m.p. 177°–178° C.

2-Benzyl-4-benzyloxy-7-methylindazole

This is obtained by the reaction of 4-benzyloxy-7-methylindazole with benzyl chloride in the presence of potassium carbonate in dimethylformamide at 80° C., in admixture with the isomeric 1-benzyl-4-benzyloxy-7-methylindazole (m.p. 92°–93° C.), as the main product which is separable by chromatography on silica gel. It is obtained in the form of colorless cyrstals; m.p. 87°–88° C.

2-Benzyl-4-hydroxy-7-methylindazole

This is obtained by the hydrogenolysis of 2-benzyl-4-benzyloxy-7-methylindazole in the presence of palladium charcoal in the form of bluish crystals; m.p. 201°–203° C.

2-Benzyl-4-(2,3-epoxypropoxy)-7-methylindazole

This is obtained, by the reaction of 2-benzyl-4-hydroxy-7-methylindazole with 2,3-epoxypropoxy p-toluenesulphonate in the presence of potassium carbonate in dimethylformamide at 60°–70° C., in the form of colorless crystals; m.p. 85°–86° C.

EXAMPLE 29

4-[3-(4-Phenoxymethylpiperidino)-propoxy]-indazole 4.4 g. 2-Benzyl-4-[3-(p-toluenesulphonyloxy)-propoxy]-indazole and 3.8 g. 4-(phenoxymethyl)-piperidine are heated with stirring for 15 hours at 60°–70° C. in 20 ml. 1,2-dimethoxyethane. The reaction mixture is then diluted with 30 ml. diethyl ether, filtered with suction and the filtrate evaporated in a vacuum. Treatment of the filtrate residue with 40 ml. 2N hydrochloric acid gives a crystalline hydrochloride. This is dissolved in methanol and hydrogenated at atmospheric pressure in the presence of palladium charcoal. After filtering off the catalyst with suction and evaporating the filtrate in a vacuum, the evaporation residue is mixed with 2N aqueous sodium hydroxide solution and taken up in methylene chloride. The solution is dried with anhydrous sodium sulphate, the solvent is removed in a vacuum and the crystalline residue is stirred with ligroin and recrystallized from methanol. There are obtained 2.1 g. (57.5% of theory) 4-[3-(4-phenoxymethylpiperidino)-propoxy]-indazole in the form of colorless leaflets; m.p. 160°–161° C.

The 2-benzyl-4-(3-p-toluenesulphonyloxypropoxy)-indazole used as starting material is obtainable as follows:

2-Benzyl-4-hydroxyindazole

The isomeric mixture of 1-benzyl-4-nitroindazole and 2-benzyl-4-nitroindazole obtained by the benzylation of 4-nitroindazole is reduced with hydrazine and Raney nickel in methanol and subsequently heated with excess sodium hydrogen sulphite in water. The 1-benzyl-4-aminoindazole (m.p. 73°–75° C.) thereby remains undissolved. Upon acidifying the solution, 2-benzyl-4-hydroxyindazole precipitates out and is obtained in the form of colorless crystals; m.p. 172°–174° C.

2-Benzyl-4-(3-hydroxypropoxy)-indazole

A mixture of 24 g. 2-benzyl-4-hydroxyindazole, 10.4 ml. 3-bromopropan-1-ol and 16 g. potassium carbonate in 100 ml. dimethylformamide is stirred for 30 hours at 70° C. After dilution with methylene chloride, the reaction mixture is filtered with suction, the filtrate is evaporated and the evaporation residue is purified chromatographically on silica gel (elution agent methylene chloride-ethyl acetate 9:1 v/v), 2-benzyl-4-(3-hydroxypropoxy)-indazole being obtained in the form of an oil.

2-Benzyl-4-(3-p-toluenesulphoxypropoxy)-indazole

Into a solution of 7.3 g. 2-benzyl-4-(3-hydroxypropoxy)-indazole, 3.6 ml. of triethylamine and 50 ml. toluene there are introduced 4.9 g. p-toluenesulphonyl chloride, dissolved in 20 ml. toluene, whereafter the reaction mixture is stirred for about 100 hours at ambient temperature. The triethylamine hydrochloride formed is filtered off with suction, the filtrate is gently evaporated in a vacuum and the evaporation residue is purified by column chromatography on silica gel (elution agent methylene chloride-ethyl acetate 9:1 v/v). By triturating the initially obtained oil with diethyl ether, there are obtained colorless crystals of 2-benzyl-4-(3-p-toluenesulphoxypropoxy)-indazole; m.p. 99°–100° C.

EXAMPLE 30

4-[2-Hydroxy-3-(4-phenoxymethylpiperidino)-propoxy]-6-tert.-butylindazole 4.2 g. 1-Acetyl-6-tert.-butyl-4-(2,3-epoxypropoxy)-indazole and 11.2 g. 4-(phenoxymethyl)-piperidine are heated under reflux for 2 hours with 50 ml. 1,2-dimethoxyethane. The reaction mixture is then evaporated and the evaporation residue is purified chromatographically on silica gel (elution agent ethyl acetate-ethanol 9:1 v/v). The oil initially obtained crystallizes upon triturating with diethyl ether-ligroin (1:1 v/v). By extractive recrystallization with diethyl ether, there are obtained 1.8 g. (28% of theory) 4-[2-hydroxy-3-(4-phenoxymethylpiperidino)-propoxy]-6-tert.-butylindazole in the form of colorless crystals; m.p. 130°–131° C.

The 1-acetyl-6-tert.-butyl-4-(2,3-epoxypropoxy)-indazole used as starting material can be prepared as follows:

2-Methyl-3-nitro-5-tert.-butylphenyl benzyl ether

This is obtained, by reacting 2-methyl-3-nitro-5-tert.-butylphenol with benzyl chloride in dimethylformamide in the presence of potassium carbonate at 80° C., in the form of yellowish crystals; m.p. 77°–79° C.

2-Methyl-3-amino-5-tert.-butylphenyl benzyl ether

This is obtained, by reducing 2-methyl-3-nitro-5-tert.-butylphenyl benzyl ether with hydrazine hydrate and Raney nickel in methanol, in the form of a pale brown oil.

2-Methyl-3-acetamido-5-tert.-butylphenyl benzyl ether

This is obtained, by acetylating 2-methyl-3-amino-5-tert.-butylphenyl benzyl ether with acetic anhydride in toluene, in the form of colorless crystals; m.p. 170°–172° C.

1-Acetyl-4-benzyloxy-6-tert.-butylindazole

This is obtained, by nitrosating and ring closure of 2-methyl-3-acetamido-5-tert.-butylphenyl benzyl ether by the action of isoamyl nitrite, sodium acetate and acetic anhydride in toluene at 80° C., in the form of colorless crystals; m.p. 73°–74° C.

1-Acetyl-4-hydroxy-6-tert.-butylindazole

This is obtained, by the hydrogenolysis of 1-acetyl-4-benzyloxy-6-tert.-butylindazole in the presence of palladium charcoal in methanol, in the form of colorless crystals; m.p. 182°–184° C.

1-Acetyl-6-tert.-butyl-4-(2,3-epoxypropoxy)-indazole

This is obtained, by the reaction of 1-acetyl-4-hydroxy-6-tert.-butylindazole with epibromohydrin and sodium hydride in dimethylformamide at ambient temperature, in the form of a colorless oil.

EXAMPLE 31

4-[2-Pivaloyloxy-3-(4-phenoxymethylpiperidino)-propoxy]-indazole

A mixture of 2.2 g. 4-[2-hydroxy-3-(4-phenoxymethylpiperidino)-propoxy]-indazole, 1.25 g. pivalic anhydride and 10 g. pivalic acid is warmed to 40° C., thereupon poured into 2N aqueous hydroxide solution, extracted with methylene chloride and the extract evaporated and recrystallized from isopropanol/water. There is obtained 1.3 g. (47% of theory) 4-[2-pivaloyloxy-3-(4-phenoxymethylpiperidino)-propoxy]-indazole in the form of colorless crystals; m.p. 116°–118° C.

The dosage schedule for blood pressure lowering is entirely dependent on the condition of the patient, e.g. a human or animal mammal, his response to the treatment and whether or not he is ambulatory or hospitalized. The treatment should be begun with small doses (100 mg) and increased gradually depending upon the patient's response. The dosage can be increased at 5 to 7 day intervals until an average daily dose of 100 to 300 mg is reached. For maintenance, two to four doses a day are usually required. The dosages for inhibition of adrenergic β-receptors are substantially the same.

In order to establish the effectiveness of the novel products of the invention a series of tests was carried out as follows:

The β-blockade activity of the substances was determined for measuring the retardation of the isoprenaline tachycardia on the one hand and, on the other hand, the vasodilation was determined by measuring the blood pressure lowering efffect.

Under local anesthesia a catheter was implanted in wakened rabbits in the middle ear artery and the ear rim vein.

In the subsequent experiment the arterial blood pressure was registered via the catheter and an electromechanical transducer (Statham P 23 Db) on a direct printer (Messrs. Schwarzer, Munich). The heart beat frequency was calculated by counting of 20 beats with rapid paper feed.

The test substances were injected intravenously into each animal by way of the catheter in dosages of 0.3, 1.0 and 3.0 mg per kg (4.3 mg/kg altogether), dissolved in isotonic sodium chloride, if necessary with the addition of e.g. dimethyl formamide as a dissolving intermediary.

The vasodilation is expressed as the maximum percentage blood pressure decrease within 30 minutes after the last injection of the test substances. Therefore, the higher the value in the left column of the table, the stronger the effect.

The β-blockade was tested by way of the antagonistic effect vis-a-vis isoprenaline. Isoprenaline was injected intravenously at a dosage of 1 μg/kg. The effect on the heart beat frequency was determined 30 seconds after the injection. The β-blockade effect is characterized by the blockage of the isoprenaline effect which amounts to 340 beats per minute without test substances. Therefore, the lower the value in the right column of the table, the stronger the effect.

The injection volume of all pharmaceuticals amounted to 0.1 ml per kg.

The median values and the median deviations of 4 to 6 individual tests are set forth in the table.

Comparison substances with a β-blocking and vasodilating activity are not known; however, it was compared with a known β-blocker, viz. 1-(isopropylamino)-3-(1-naphthyloxy)-2-propanol (Propranolol).

| ACTIVITY UPON ADMINISTRATION OF 4.3 mg/kg i.v. | | |
|---|---|---|
| Active Material of Example | % Blood Pressure Drop | β-blockade |
| Control 10% DMF-NaCl | −6 ± 6 | 381 ± 7 |
| Propanolol | 4 ± 3 | 210 ± 6 |
| 1 | 14 ± 3 | 213 ± 13 |
| 2(a); 5 | 12 ± 5 | 231 ± 13 |
| 2(h) | 18 ± 2 | 244 ± 20 |

-continued

ACTIVITY UPON ADMINISTRATION OF 4.3 mg/kg i.v.

| Active Material of Example | % Blood Pressure Drop | β-blockade |
| --- | --- | --- |
| 2(m) | 5 ± 4 | 201 ± 17 |
| 6 | 15 ± 6 | 226 ± 9 |
| 9 | 12 ± 4 | 191 ± 11 |
| 11 | 5 ± 8 | 260 ± 6 |
| 12(a) | 7 ± 4 | 233 ± 18 |
| 19 | 13 ± 3 | 260 ± 10 |
| 21 | 13 ± 14 | 236 ± 22 |
| 23; 25 | 14 ± 3 | 204 ± 14 |
| 24(a) | 8 ± 4 | 180 ± 8 |
| 24(b) | 27 ± 8 | 183 ± 20 |
| 24(c) | 16 ± 3 | 226 ± 15 |
| 24(f) | 12 ± 3 | 230 ± 17 |
| 28 | 10 ± 2 | 183 ± 16 |

The present invention also provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example olive oil.

It will be understood that the specification and examples are illustrative but not limitative of the present invention and that other embodiments within the spirit and scope of the invention will suggest themselves to those skilled in the art.

What is claimed is:

1. A 3-(4-phenoxymethylpiperidino)-propylphenyl-ether of the formula

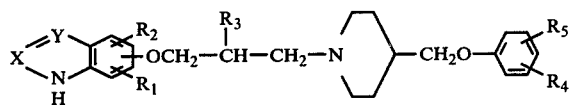

wherein
$R_1$ and $R_2$ each independently is hydrogen, lower alkyl, hydroxyalkyl, lower alkanoyloxyalkyl or —CO-Z,
Z is hydroxy, lower alkyloxy or

$R_6$ and $R_7$ each independently is hydrogen, lower alkyl or hydroxyalkyl,
$R_3$ is hydrogen or —O-$R_8$,
$R_8$ is hydrogen, lower alkanoyl or benzoyl optionally substituted by halogen, lower alkyl, lower alkoxy, alkoxycarbonyl, hydroxyl, alkylthio, nitrile, nitro or trifluoromethyl,
$R_4$ and $R_5$ each independently is hydrogen, halogen, hydroxy, benzyloxy, lower alkyl, lower alkoxy, lower alkylthio, carboxy, benzyloxycarbonyl or lower alkoxycarbonyl,
X and Y, each independently is nitrogen or

$R_9$ is hydrogen, lower alkyl optionally substituted by —O-$R_8$, or —CO-Z, or a pharmacologically acceptable salt thereof.

2. A compound according to claim 1, wherein the several alkyl, hydroxyalkyl, alkoxy and alkylthio moieties have up to 4 carbon atoms and, the alkanoyl moieties have up to 6 carbon atoms.

3. A compound according to claim 1, wherein X is

and Y is nitrogen.

4. A compound according to claim 1, wherein X is nitrogen and Y is

5. A compound according to claim 1, wherein such compound is 4-[2-hydroxy-3-(4-phenoxymethyl-piperidino)propoxy]-indole.

6. A compound according to claim 1, wherein such compound is 4-{2-hydroxy-3-[4-(3-chlorophenoxyme-thyl)-piperidino]-propoxy}-indole benzoate.

7. A compound according to claim 1, wherein such compound is 4-[2-hydroxy-3-(4-phenoxymethyl-piperidino)-propoxy]-indazole.

8. A compound according to claim 1, wherein such compound is 4-{2-hydroxy-3-[2-methylphenoxyme-thyl)-piperidino]-propoxy}-indazole.

9. A compound according to claim 1, wherein such compound is 4-{2-hydroxy-3-[4-(3-methylphenoxyme-thyl)-piperidino]-propoxy}-indazole.

10. A blood pressure lowering and adrenergic β-receptor inhibiting composition comprising a blood pressure lowering and adrenergic β-receptor inhibiting effective amount of a compound or salt according to claim 1 in admixture with a pharmacologically acceptable diluent.

11. The method of lowering the blood pressure of a patient which comprises administering to said patient a blood pressure lowering effective amount of a compound or salt according to claim 1.

12. The method of inhibiting the adrenergic β-receptors of a patient which comprises administering to said patient an adrenergic β-receptor inhibiting effective amount of a compound or salt according to claim 1.

* * * * *

UNITED STATES PATENT AND TRADEMARK OFFICE
CERTIFICATE OF CORRECTION

PATENT NO. : 4,146,630
DATED : March 27,1979
INVENTOR(S) : Wolfgang Kampe et al

It is certified that error appears in the above-identified patent and that said Letters Patent are hereby corrected as shown below:

Col. 12, line 10    "29% should be "28%".

Col. 23, line 55    After "benzoyl" insert "or naphthoyl".

Signed and Sealed this

Nineteenth Day of May 1981

[SEAL]

*Attest:*

RENE D. TEGTMEYER

*Attesting Officer*    *Acting Commissioner of Patents and Trademarks*